(12) United States Patent
Tanaka

(10) Patent No.: US 10,145,806 B2
(45) Date of Patent: Dec. 4, 2018

(54) X-RAY APPARATUS

(71) Applicant: NIKON CORPORATION, Tokyo (JP)

(72) Inventor: Toshihisa Tanaka, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 274 days.

(21) Appl. No.: 15/103,031

(22) PCT Filed: Dec. 12, 2013

(86) PCT No.: PCT/JP2013/083371
§ 371 (c)(1),
(2) Date: Jun. 9, 2016

(87) PCT Pub. No.: WO2015/087432
PCT Pub. Date: Jun. 18, 2015

(65) Prior Publication Data
US 2016/0377558 A1   Dec. 29, 2016

(51) Int. Cl.
*H05G 1/02* (2006.01)
*G01N 23/04* (2018.01)

(52) U.S. Cl.
CPC ....... *G01N 23/04* (2013.01); *G01N 2223/308* (2013.01); *G01N 2223/33* (2013.01)

(58) Field of Classification Search
CPC ......... G01N 2223/308; G01N 2223/33; G01N 23/04; G01N 2035/0036
See application file for complete search history.

(56) References Cited

U.S. PATENT DOCUMENTS

| 5,473,657 A | 12/1995 | McKenna |
| 5,493,594 A | 2/1996 | Hamada et al. |
| 5,784,428 A | 7/1998 | Schmidt |
| 2008/0232551 A1* | 9/2008 | Peecock ............... G01N 23/207 378/195 |

FOREIGN PATENT DOCUMENTS

| JP | 10-057368 A | 3/1998 |
| JP | 2001-128962 A | 5/2001 |
| JP | 2007-255951 A | 10/2007 |
| JP | 2010-243169 A | 10/2010 |
| JP | 2011-024866 A | 2/2011 |
| WO | WO 2006/003430 A1 | 1/2006 |
| WO | WO 2013/002800 A1 | 1/2013 |

OTHER PUBLICATIONS

Office Action issued by Japanese Patent Office dated May 2, 2017 in counterpart Application No. 2015-552260, and English translation thereof.

(Continued)

*Primary Examiner* — Don Wong
(74) *Attorney, Agent, or Firm* — Finnegan, Henderson, Farabow, Garrett & Dunner LLP

(57) ABSTRACT

An X-ray apparatus includes: an X-ray source that radiates X-rays upon an object to be measured; a frame upon which the X-ray source is mounted; an anti-vibration mechanism that attenuates vibration applied to the frame; and a shift mechanism that shifts the frame and the anti-vibration mechanism integrally together.

9 Claims, 7 Drawing Sheets

(56) References Cited

OTHER PUBLICATIONS

European Search Report issued by European Patent Office dated Sep. 12, 2017 in counterpart Application No. 13898946.2. XP-002773296.
Notification of Reason(s) for Refusal issued by the Japanese Patent Office in Japanese Patent Application No. 2015-552260, Dispatch No. 030372, dated Jan. 30, 2018.
International Search Report issued by the International Bureau of WIPO in Japanese Application No. WO 2015/087432 (PCT/JP2013/083371), dated Apr. 14, 2016.
Office Action dated Jul. 12, 2018, by the Taiwanese Patent Office in counterpart Taiwanese Patent Application No. 103142337, and the English translation thereof.

* cited by examiner

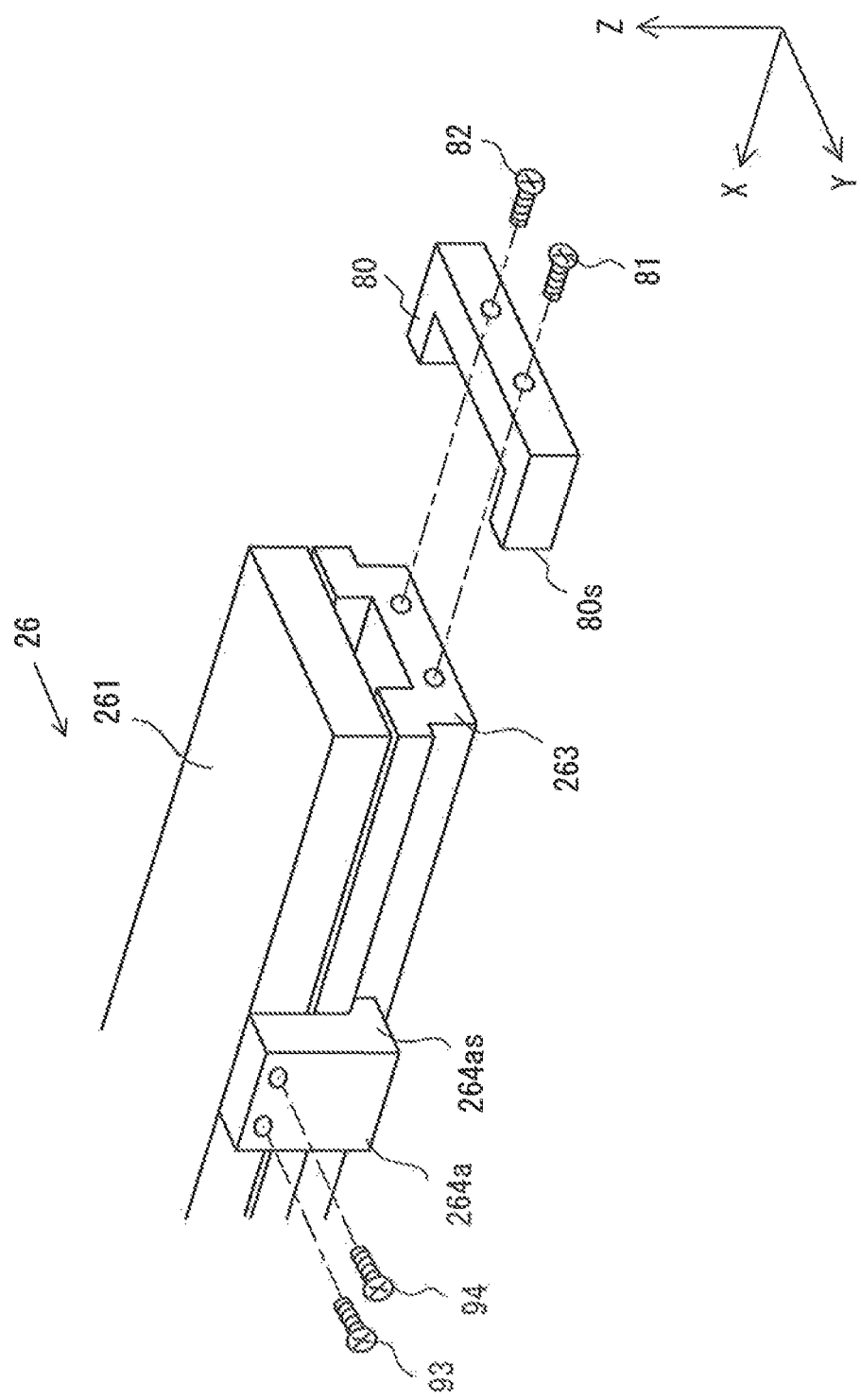

X-RAY APPARATUS

TECHNICAL FIELD

The present invention relates to an X-ray apparatus.

BACKGROUND ART

An X-ray inspection apparatus that has a frame (i.e. a stand) to which at least an X-ray tube is attached, for inspection or the like, is per se known as the prior art (for example, refer to Patent Document #1).

CITATION LIST

Patent Literature

Patent Document #1: U.S. Pat. No. 5,493,594.

SUMMARY OF INVENTION

Technical Problem

With the X-ray inspection apparatus of Patent Document #1 mentioned above, a shift mechanism is required for pulling out the X-ray source from the chamber, in order for maintenance to be performed upon the X-ray source. However, since such a shift mechanism is provided between the frame and an anti-vibration mounting, accordingly it is not possible to attenuate vibration sufficiently, and there has been the problem that it has not been possible to obtain accurate X-ray measurement results.

Solution to Technical Problem

According to the 1st aspect of the present invention, an X-ray apparatus comprises: an X-ray source that radiates X-rays upon an object to be measured; a frame upon which the X-ray source is mounted; an anti-vibration mechanism that attenuates vibration applied to the frame; and a shift mechanism that shifts the frame and the anti-vibration mechanism integrally together.

According to the 2nd aspect of the present invention, it is preferred that in the X-ray apparatus according to the 1st aspect, the frame further comprises: a stage upon which the object to be measured is mounted; and an X-ray detector that detects X-rays that have been radiated from the X-ray source and that have passed through the object to be measured.

According to the 3rd aspect of the present invention, the X-ray apparatus according to the 2nd aspect may further comprise: a base plate that supports the shift mechanism, and wherein: the shift mechanism supports the frame via the anti-vibration mechanism.

According to the 4th aspect of the present invention, it is preferred that in the X-ray apparatus according to the 1st aspect, the shift mechanism comprises: a guide rail; and a plurality of shift members that relatively shift along the guide rail; and wherein: the shift members are positioned below the anti-vibration mechanism in the vertical direction.

According to the 5th aspect of the present invention, it is preferred that in the X-ray apparatus according to the 4th aspect, the shift mechanism is adapted so that a leg member for supporting the frame can be installed below the shift member.

According to the 6th aspect of the present invention, it is preferred that in the X-ray apparatus according to the 5th aspect, the shift mechanism comprises a regulation member that, when the leg member is to be installed, temporarily regulates shifting of the frame to a position at a predetermined shift amount within the total shiftable amount of the frame.

According to the 7th aspect of the present invention, the X-ray apparatus according to the 4th aspect may further comprise: a chamber that houses the frame, and wherein: the base plate constitutes a portion of the chamber; and in a position in which the frame has been shifted by a predetermined shift amount, at least a portion of the frame is exposed from the chamber.

According to the 8th aspect of the present invention, it is preferred that in the X-ray apparatus according to any one of the 1st through 7th aspects, the anti-vibration mechanism is provided more inward upon a lower surface of the frame than an outer edge portion of the lower surface of the frame.

According to the 9th aspect of the present invention, the X-ray apparatus according to any one of the 2nd through 8th aspects may further comprise: a reconstruction unit that calculates the internal structure of the object to be measured on the basis of projection images of the object to be measured obtained when X-rays have passed through the object to be measured from a plurality of different directions while changing a relative position of the X-ray detector and the object to be measured.

Advantageous Effect of Invention

Since, according to the present invention, the shift mechanism is capable of shifting the frame upon which the X-ray source is mounted and the anti-vibration mechanism that attenuates vibration applied to the frame integrally with one another as one unit, accordingly it is possible satisfactorily to attenuate vibration applied to the frame via the shift mechanism from the exterior, and thus it is possible to provide an X-ray apparatus that experiences less influence due to vibration.

BRIEF DESCRIPTION OF DRAWINGS

FIG. 7 is a perspective view for explanation of the external appearance of a shift control structure.

DESCRIPTION OF EMBODIMENTS

In the X-ray apparatus according to this invention, a shift mechanism is housed within a chamber and integrally shifts both a frame on which are mounted a stage upon which an object to be measured is mounted, an X-ray source, and an X-ray detector, and also an anti-vibration mechanism that attenuates vibration applied to the frame. In detail, this X-ray apparatus is constructed so that it becomes possible to pull out the frame to the exterior during maintenance and inspection of various units mounted to the frame. One aspect of the present invention is an apparatus that makes the goals of simple and easy maintenance and servicing and of enhanced accuracy of X-ray measurement compatible with one another by implementing a construction for an X-ray apparatus that is capable of reducing the negative influence upon the results of measurement of an object to be measured by X-rays due to vibration from outside the chamber, or due to transmitting vibration, which is generated under the influence of vibration from the outside the chamber by a shift mechanism that is provided for performing pulling out of the frame, to the frame. In the following, this will be explained in detail.

Embodiment

An X-ray apparatus according to an embodiment of the present invention will now be explained with reference to the drawings. This X-ray apparatus is an X-ray CT inspection apparatus that irradiates X-rays upon an object to be measured, and that acquires internal information about that object to be measured (for example, details of its interior structure) and so on in a non-destructive manner by detecting transmitted X-rays that have passed through the object to be measured. When this object that is being subjected to measurement is, for example, an industrial component such as a mechanical or electronic component or the like, then the X-ray apparatus may be termed an X-ray CT inspection apparatus for industrial use.

Furthermore, this embodiment is explained in order for the gist of the present invention to be understood in concrete terms; the present invention is not to be considered as being limited in any way thereby, provided that there is no specification.

Figure 1:
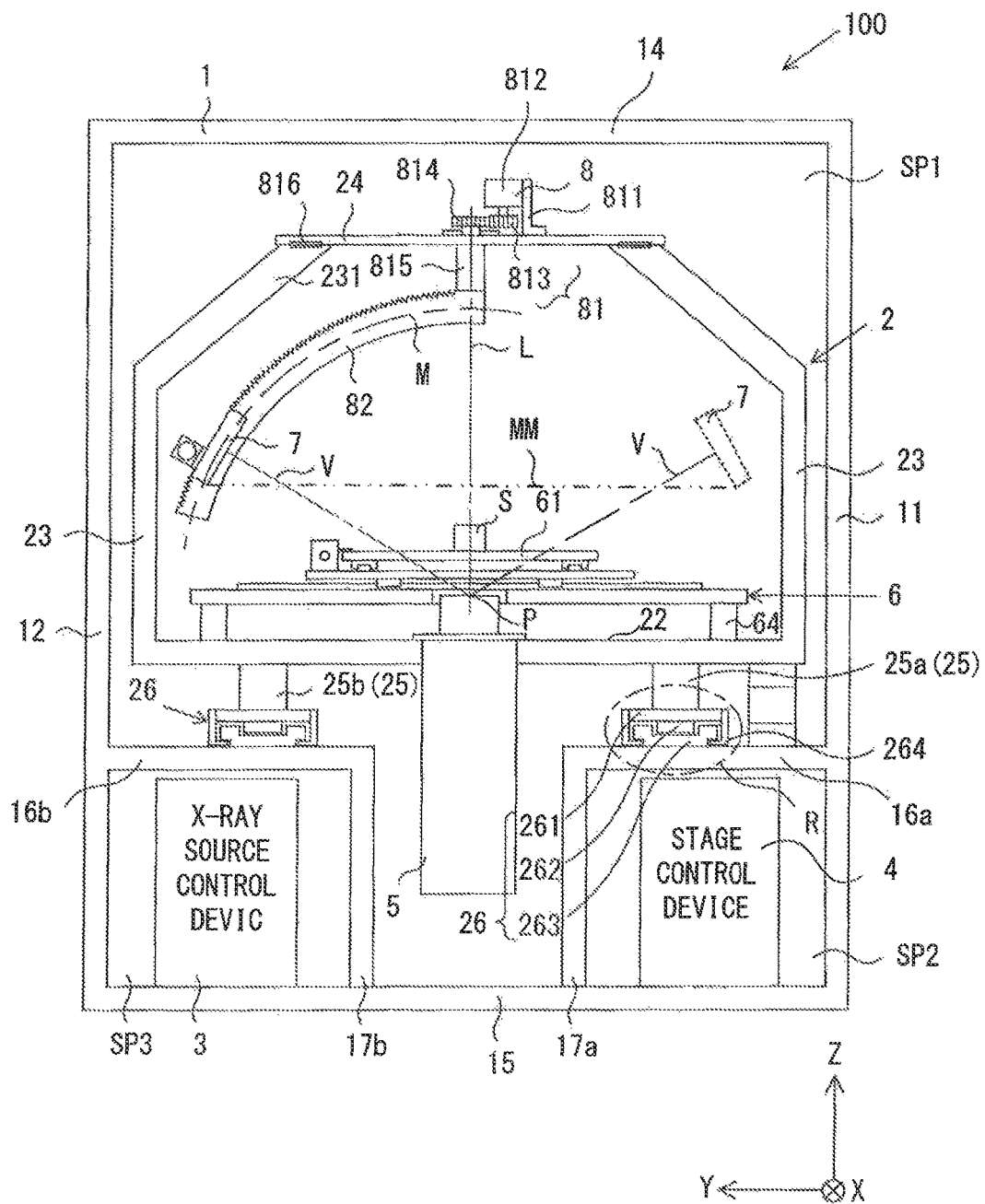
FIG. 1 is an internal elevation view of an X-ray apparatus according to an embodiment of the present invention.
Figure 2:
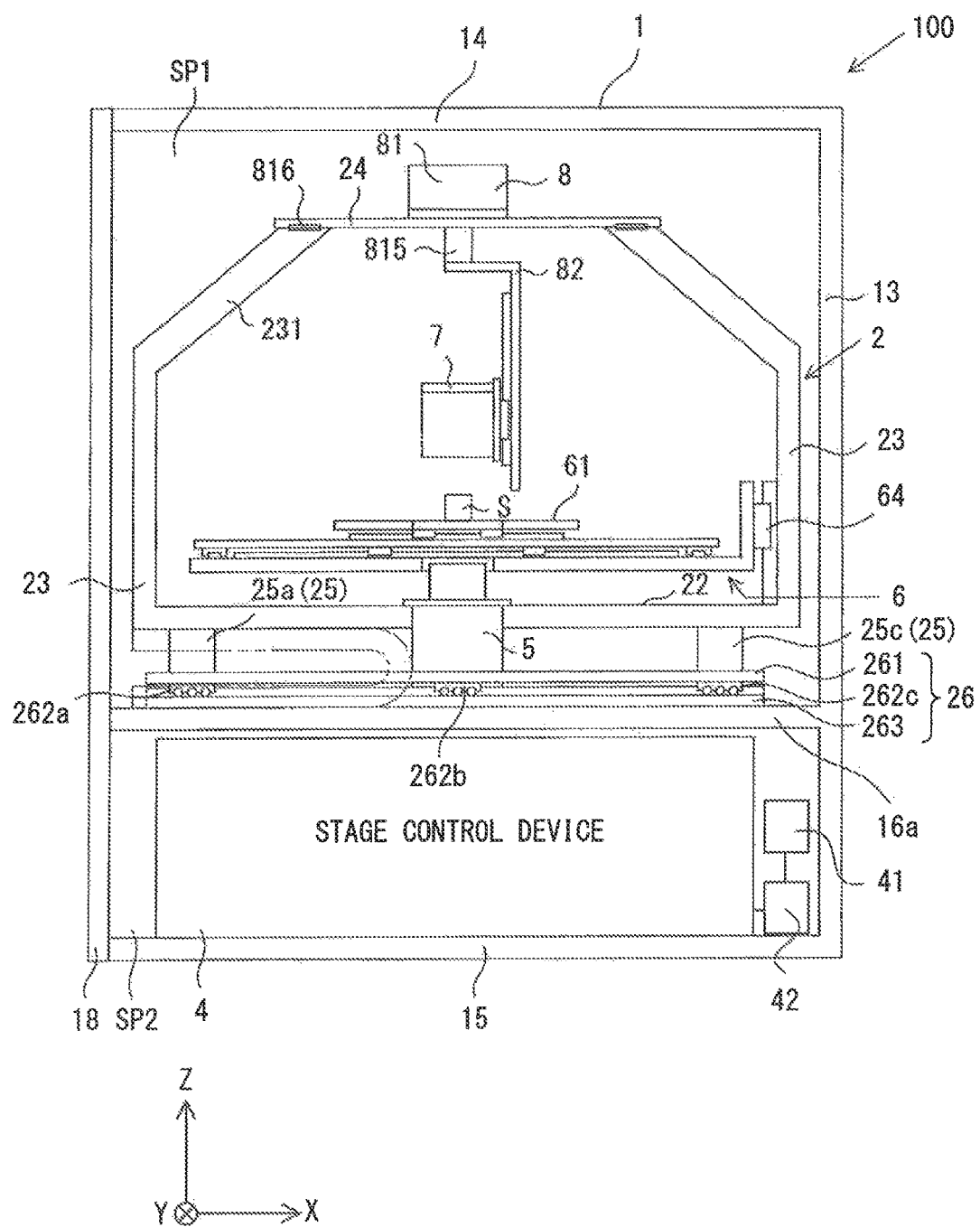
FIG. 2 is an internal side view of this X-ray apparatus according to an embodiment of the present invention.
Figure 3:
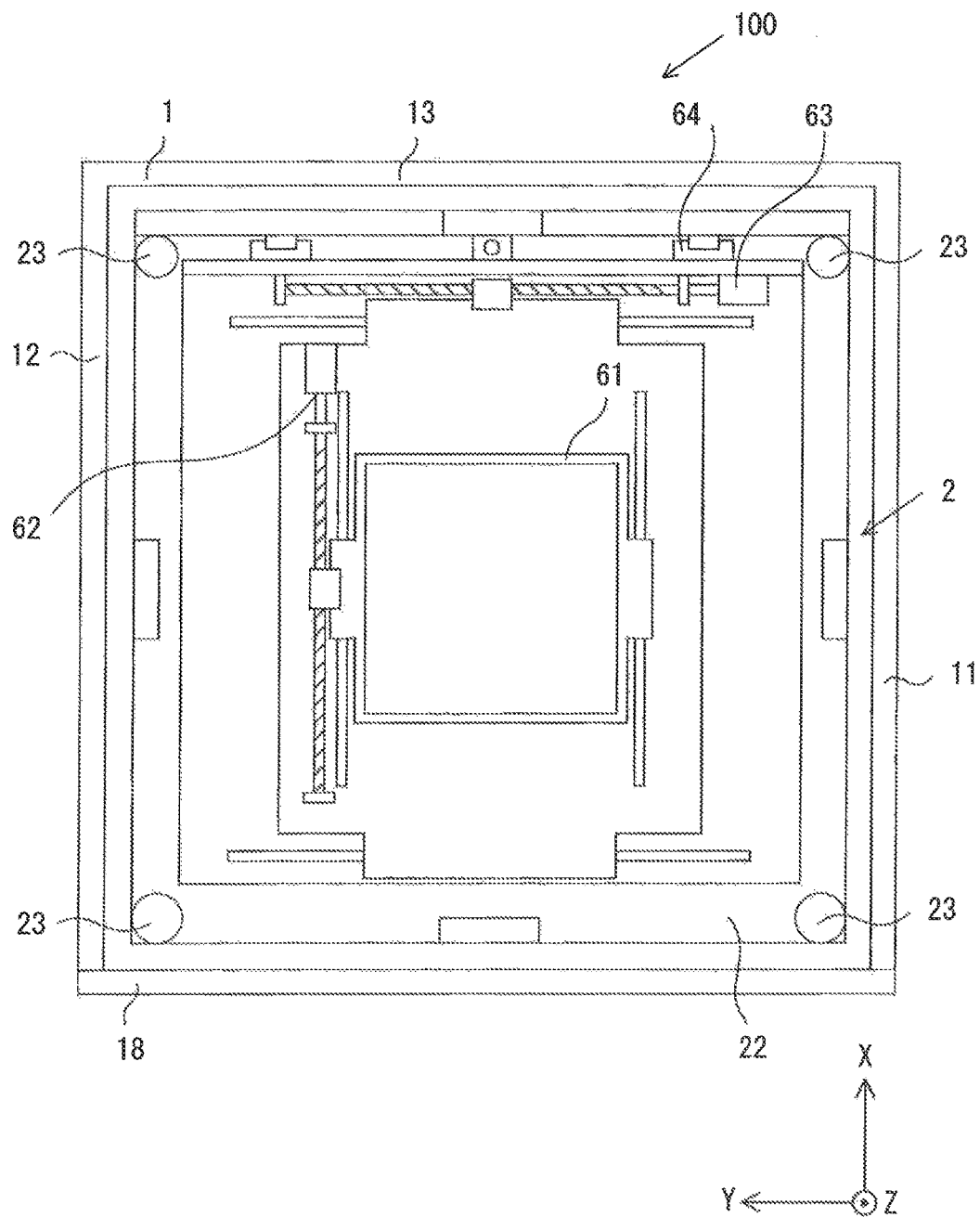
FIG. 3 is an internal plan view of this X-ray apparatus according to an embodiment of the present invention.
Figure 4:
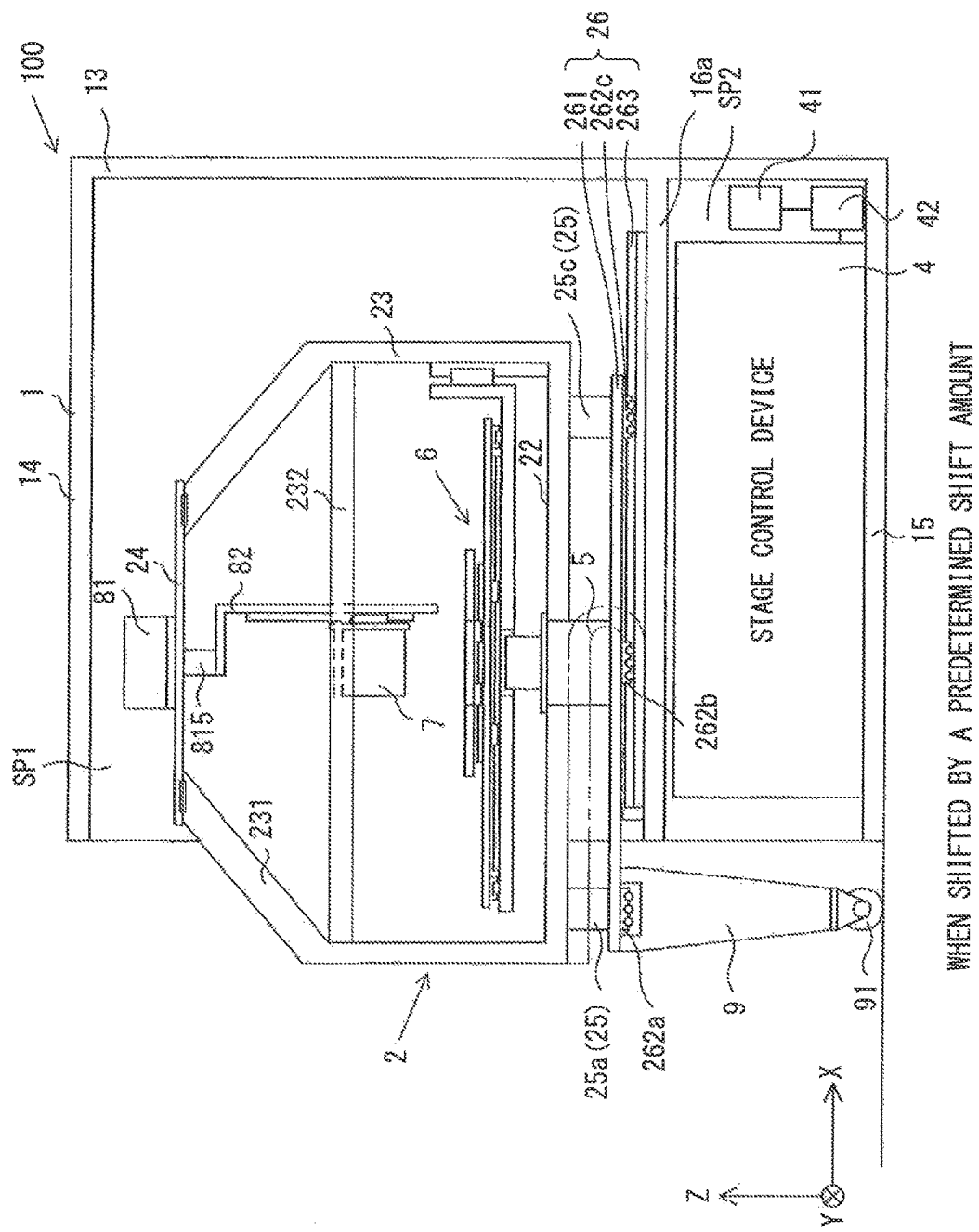
FIG. 4 is a side view when a frame that is housed in the interior of the chamber has been pulled out from the chamber to the exterior by just a predetermined shift amount.
Figure 5:
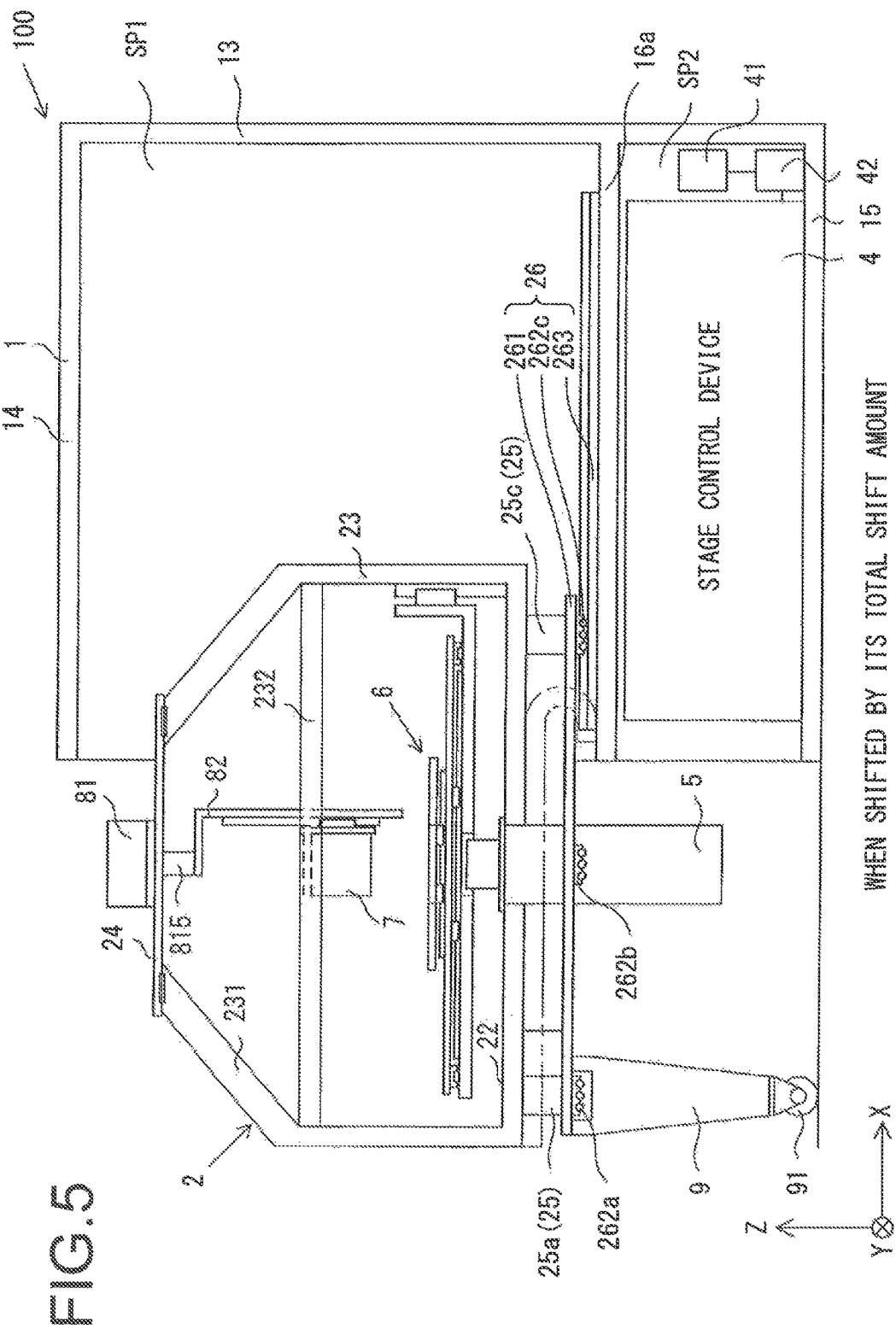
FIG. 5 is a side view when this frame that is housed in the interior of the chamber has been pulled out from the chamber to the exterior up to its shifting limit.

FIGS. 1 through 5 are figures showing an example of the internal structure of the X-ray apparatus 100 according to this embodiment; FIG. 1 is an internal elevation view of the X-ray apparatus 100; FIG. 2 is an internal side view of the X-ray apparatus 100; FIG. 3 is an internal plan view of the X-ray apparatus 100; FIG. 4 is a side view when a frame that is held in the interior of the chamber has been pulled out to the exterior of the chamber by just a predetermined shift amount; and FIG. 5 is a side view when this frame that is held in the interior of the chamber has been pulled out to the exterior of the chamber to its shifting limit. It should be understood that, for the convenience of explanation, a coordinate system is established having X axis and Y axis as shown in the figures and Z axis along the vertical direction.

The X-ray apparatus 100 comprises the chamber 1, the frame 2, an X-ray source control device 3, and a stage control device 4. The chamber 1 is disposed upon the floor surface of a workplace or the like so as to be substantially parallel to the X-Y plane (i.e., horizontal), with the frame 2, the X-ray source control device 3, and the stage control device 4 being housed therein. The chamber 1 has a hollow box shaped construction comprising outer wall surfaces 11, 12 that are substantially parallel to the X-Z plane, an outer wall surface 13 (refer to FIG. 2) that is substantially parallel to the Y-Z plane, an upper wall surface 14, a first bottom surface 15, and a door 18 (refer to FIG. 2). The door 18 is attached to one of the minus X axis side edge portions of the outer wall surface 11 or 12, to the upper wall surface 14, or to the first bottom surface 15, and is fitted so as to be capable of being opened and closed. Second bottom surfaces 16a, 16b (generically referred to by the reference symbol 16) that extend substantially parallel to the X-Y plane are provided in the interior of the chamber 1, and inner wall surfaces 17a, 17b (generically referred to by the reference symbol 17) that support the second bottom surfaces 16a, 16b respectively are attached to the first bottom surface 15.

The frame 2 is mounted so as to be shiftable along the X axis direction from the space SP1 shown in the figures to the exterior of the chamber 1. The frame 2 is shiftably mounted upon the second bottom surfaces 16. The stage control device 4 is contained within a space SP2 that is defined below the second bottom surface 16a, and the X-ray source control device 3 is contained within a space SP3 that is defined below the second bottom surface 16b. The X-ray source control device 3 and the stage control device 4 are respectively electrically connected by cables to an X-ray source 5 and to a mounting unit 6 that will be described hereinafter. In order to ensure that X-rays should not leak to the exterior of the chamber 1, the various components from which the chamber 1 is assembled contains lead as a material. It should be understood that, among the various components from which the chamber 1 is assembled, it would be sufficient for lead to be contained as a material in, at least, the portions that surround the space SP1.

The X-ray source 5, the mounting unit 6, an X-ray detector 7, and an X-ray detector drive unit 8 are mounted upon the frame 2. The frame 2 comprises a bottom base plate 22 that is shaped as rectangular, four struts 23 that are provided at the four corners of the bottom base plate 22 and that extend upward in the Z axis direction, auxiliary struts 231 that extend from the tops of the struts 23, and an attachment member 24 that is provided upon the tops of the auxiliary struts 231 for attachment of the X-ray detector drive unit 8. It should be understood that a construction in which the auxiliary struts 231 were not provided, and in which the attachment member 24 was fixed to the upper portions of the struts 23, would also be included as one aspect of the present invention. Moreover, in FIGS. 4 through 6, a situation is shown in which strength is ensured by the provision of reinforcement members 232 that link between adjacent ones of the struts 23. The details of the structure of the frame 2 will be described and explained hereinafter.

The X-ray source 5 is attached to the bottom base plate 22 of the frame 2, and hangs downward from near the central portion of the bottom base plate 22. The X-ray source 5 is controlled by the X-ray source control device 3, and irradiates X-rays that spread over a range V-V in the shape of a wide angle cone from a point of emission P shown in FIG. 1. The point of emission and the focal point of the X-ray source 5 coincide. The portion of the X-ray source 5 that hangs downward from the bottom base plate 22 is disposed in a space between the mutually opposing inner wall surfaces 17a and 17b. It should be understood that, in the following explanation, an axis passing through the point P and parallel to the Z axis direction will be termed the reference axis L. In this embodiment, the X-ray source 5 is provided so that the reference axis L passes through the center of the frame 2.

The X-ray source 5 radiates X-rays of at least one type, such as for example ultra-soft X-rays of around 50 eV, soft X-rays of around 0.1 to 2 keV, X-rays of around 2 to 20 keV, or hard X-rays of around 20 to 100 keV. It should be understood that the X-ray source 5 could incorporate a transmission type X-ray source, or could incorporate a reflection type X-ray source.

The mounting unit 6 is provided more toward the plus Z axis side than the emission point P of the X-ray source 5, and comprises a stage 61 for mounting an object to be measured S, and an X axis shift mechanism 62, a Y axis shift mechanism 63, and a Z axis shift mechanism 64 for shifting the stage 61 (refer to FIG. 3). Each of the X axis shift mechanism 62 and the Y axis shift mechanism 63 comprises a motor, a rail, a slider, and so on, and, according to control from the stage control device 4, they shift the stage 61 along the X axis direction and the Y axis direction respectively. And the Z axis shift mechanism 64 comprises a motor, a rail, a slider, and so on, and, according to control from the stage control device 4, shifts the stage 61 along the Z axis direction.

The X-ray detector 7 comprises a per se known scintillator unit including a scintillation substance, a light reception unit such as a photomultiplier tube, and so on, and receives X-rays including transmitted X-rays emitted from the X-ray source 5 that have passed through an object to be measured S that is mounted upon the stage 61. This X-ray detector 7 converts incident X-rays to optical energy, and then converts that optical energy to electrical energy, which is then outputted as electrical signals. It should be understood that it would also be acceptable to arrange for the X-ray detector 7 not to convert the incident X-rays to optical energy, but rather to electrical signals that are outputted. Moreover, the X-ray detector 7 has a plurality of pixels, and these pixels are arranged in a two-dimensional array. Due to this, it is possible to acquire the intensity distribution of the X-rays emitted from the X-ray source 5 that have passed through the entire mass of the object to be measured S, all in one operation. Accordingly, it is possible to acquire a projected image of the entire mass of the object to be measured S with a single photographic shot.

The X-ray detector drive unit 8 shifts the X-ray detector 7 along a circular track M whose center is the reference axis L. The X-ray detector drive unit 8 comprises a rotation mechanism 81 that is attached to the attachment member 24 of the frame 2, and a circular arcuate stage 82 shaped as a circular arc that is rotated by the rotation mechanism 81. The rotation mechanism 81 comprises an attachment plate 811, a motor 812 that is attached to the attachment plate 811, a first gear 813 that is rotated by the motor 812, a second gear 814 that is meshed with the first gear 813, and a hollow rotation shaft 815. By the rotation shaft 815 being rotated by the second gear 814 around the reference axis L as center, the circular arcuate stage 82 that is fixed to the lower portion of the rotation shaft 815 is rotated, and thereby the X-ray detector 7, which is provided upon the circular arcuate stage 82 so as to be shiftable therealong, is revolved along a rotation path MM around the reference axis L as center. Since the rotation shaft 815 has a hollow structure, a cable or the like (not shown in the figures) for the X-ray detector 7 can be passed through the interior of the rotation shaft 815.

An alignment mechanism 816 comprises screws or the like, and, when the job of alignment is to be performed, a straight rod shaped member that functions as an adjustment jig is passed through the interior of the rotation shaft 815, and the lower end of this jig and the point P are brought to the state of coinciding with one another. By doing this, the tilting, the shifting, and the height of the attachment member 24 may be minutely adjusted so that the rotation axis of the rotation shaft 815 and the reference axis L agree with one another. With this alignment mechanism 816 it is possible to keep the distance between the emission point P of the X-ray source 5 and the X-ray detector 7 to its predetermined design value, and, with a simple structure, it is possible to perform management of the accuracy by which the object to be measured S is measured.

The circular arcuate stage 82 is a plate that is formed in a predetermined circular arcuate length around the point P as center, this being the X-ray emission point. A guide rail and a slider and a like are provided to this circular arcuate stage 82, and the X-ray detector 7 described above is attached upon the circular arcuate stage 82 so as to be shiftable along its arcuate shape by a motor or the like. Thus, the X-ray detector 7 can be shifted along the circular arcuate track M whose center is the X-ray emission point P. Due to this, by rotating the circular arcuate stage 82 with the rotation mechanism 81, it becomes possible to perform adjustment so that the track of the X-ray detector 7 moves around the outline of the bottom surface of a cone whose vertex is the point P i.e. so that the detector is moved in a circular motion at any desired uniform height (i.e. so that it is moved around upon a surface of uniform height on the plus side of the Z axis). It should be understood that a structure in which the X-ray detector 7 is shiftable between the circular arcuate stage 82 and a plate that is formed as an arc that is parallel to and concentric with the circular arcuate stage 82 should also be included as one aspect of the present invention.

Since, by providing the structure described above with the rotation track MM having the reference axis L as center and the circular arcuate track M having the X-ray emission point P as center, it is possible to shift the detector to any desired location upon a spherical surface having the X-ray emission point P of the X-ray detector 7 as center, accordingly it is possible to photograph the object to be measured S from any photographic position and at any photographic angle desired by the user. Moreover, by shifting the stage 61 in the direction of the Z axis, it is possible to photograph the object to be measured S at any desired magnification ratio.

Figure 6:
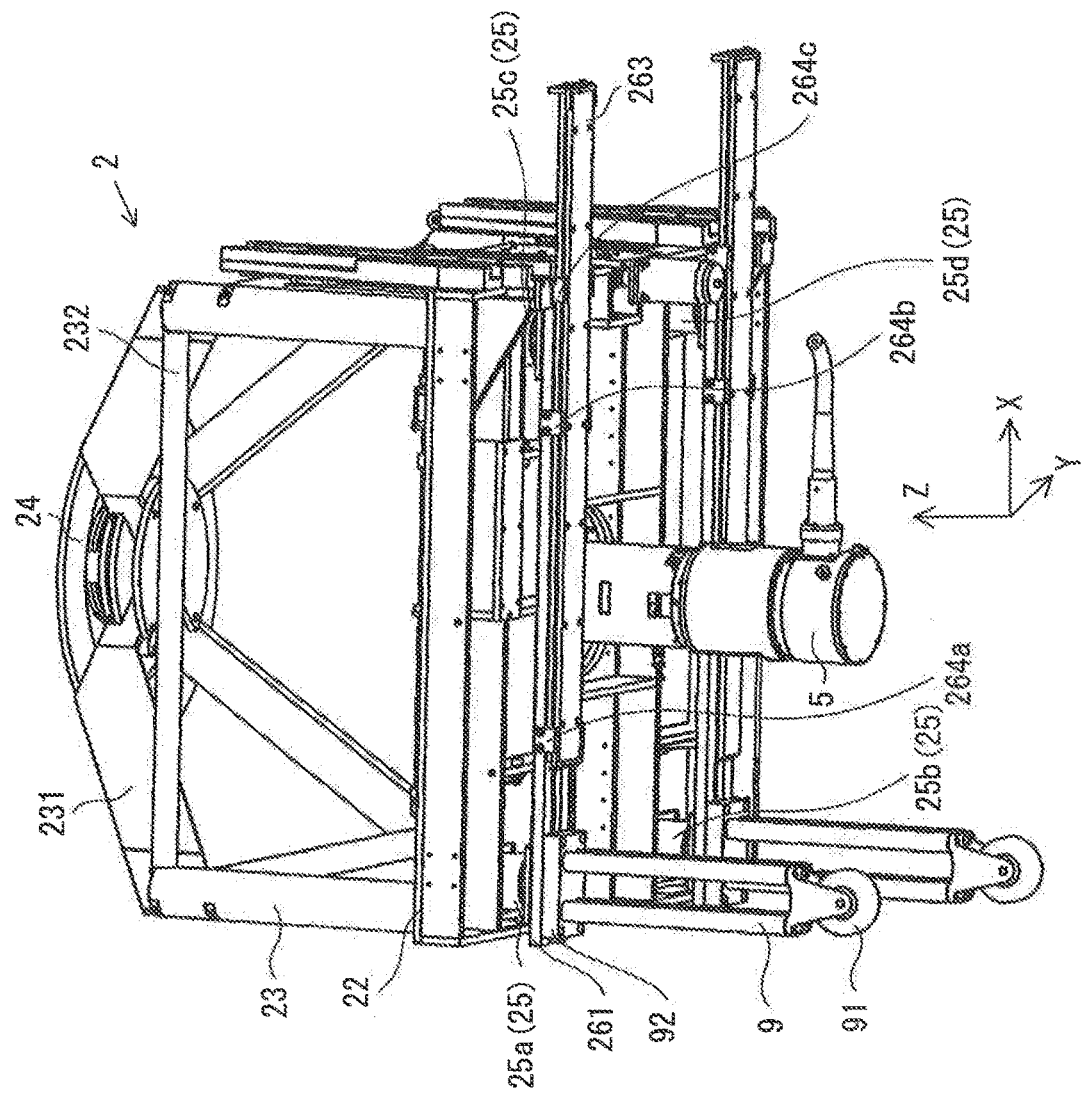
FIG. 6 is a perspective view showing the frame as seen from underneath.

The frame 2 will now be described in detail with reference to FIGS. 6 and 7. FIG. 6 is a perspective view showing the frame 2 as seen from below, and FIG. 7 is a perspective view for explanation of a mechanism for temporarily restraining shifting when the frame 2 is being shifted. It should be understood that an X-Y-Z coordinate system is established in FIGS. 6 and 7, similar to the coordinate system in FIGS. 1 through 5. Moreover in FIG. 6, for the convenience of illustration, the X-ray detector 7 and the X-ray detector drive unit 8 are omitted.

As described above, the mounting unit 6 and the X-ray detector 7 and the X-ray detector drive unit 8 (in FIG. 6 these are omitted, as described above), which are supported via the struts 23 and the attachment member 24, are provided upon the upper portion (i.e., on the plus Z axis side) of the bottom base plate 22 of the frame 2. The X-ray source 5 is attached so as to hang downward from an opening in the vicinity of the central portion of the bottom base plate 22. Anti-vibration mounts 25 are attached to the lower portion to the minus Z axis side) of the bottom base plate 22, for attenuating vibration applied to the frame 2 from the exterior of the chamber 1 via the second bottom surface 16. These anti-vibration mounts 25 are made to incorporate, for example, per se known air springs or coil springs or the like, either singly or in combination.

In this embodiment, an example is shown in which four of these anti-vibration mounts 25a, 25b, 25c, and 25d are provided (the reference symbol 25 is used to refer to them generically). Each of the anti-vibration mounts 25 is disposed somewhat inward from the circumference edge portion of the bottom base plate 22 of the frame 2. The X-ray source 5 is positioned within a rectangular area that is surrounded by straight lines passing through and connecting the centers of attachment of the four anti-vibration mounts 25a, 25b, 25c, and 25d to the bottom base plate 22. It should be understood that while, in this embodiment, an example is shown in which four of the anti-vibration mounts 25 are provided, the number of the anti-vibration mounts 25 should not be considered as being limited to four; it is desirable to provide an optimum number thereof, according to the size and the weight of the frame 2. Moreover, the anti-vibration mounts 25 are adapted to be capable of attenuating vibrational displacement in all directions, thus constituting movable mechanisms that allow displacement in all directions and also dampers that attenuate motion generated in that movable mechanism.

Each of the anti-vibration mounts 25 is fixed to an upper attachment plate 261 that is included in a shift mechanism 26 provided at its lower end (i.e. at its minus Z axis end) (in other words, each of the mounts is fixed directly or indirectly to the shifting side of that shift mechanism). And a lower guide rail 263 included in the shift mechanism 26 is attached to one of the second bottom surfaces 16 of the chamber, in other words the fixed side, so that the shift mechanism 26 allows the frame 2 and the anti vibration mount 25 to shift integrally with one another with respect to the second bottom surface 16, which serves as a base plate.

In this embodiment two shift mechanisms 26 are provided, with one of these shift mechanisms 26 being attached to the lower portions of the anti-vibration units 25a, 25c, while the other shift mechanism 26 is attached to the lower portions of the anti-vibration units 25b, 25d. One of the shift mechanisms 26 is disposed upon the second bottom surface 16a, while the other shift mechanism 26 is disposed upon the second bottom surface 16b.

Each of the shift mechanisms 26 comprises an upper attachment plate 261, roller units 262 (refer to FIGS. 4 and 5), a lower guide rail 263, and a shift control structure 264. The upper attachment plate 261 of one of the shift mechanisms 26 is attached to the lower surfaces of the anti-vibration mounts 25a, 25c, while the upper attachment plate 261 of the other shift mechanism 26 is attached to the lower surfaces of the anti-vibration mounts 25b, 25d, with the two upper attachment plates 261 both extending along the X axis direction. The plurality of roller units 262 are fitted to the lower surfaces of the upper attachment plates 261. In this embodiment, an example is shown in which three of the roller units 262a, 262b, and 262c are thus attached on each side. The roller units 262a, 262c are provided so that the central axes in the vertical direction (i.e. in the Z axis direction) of the anti-vibration mounts 25a, 26c pass through the centers of those roller units 262a, 262c respectively. In other words, it is desirable that the anti-vibration units 25a, 25c should be arranged directly above the roller units 262a, 262c respectively. However, it should be understood that the central axes of the anti-vibration mounts 25a, 25c are not to be considered as being necessarily limited to passing through the centers of the roller units 262a, 262c. Moreover, neither is the number of roller units 262 provided to the shift mechanisms 26 necessarily limited to being three; it is desirable for an optimum number thereof to be provided, according to the size and weight of the frame 2.

The lower guide rails 263 are attached to the second bottom surfaces 16 of the chamber 1 so as to extend along the X axis direction, and their cross sections in planes parallel to the Y-Z plane have letter-U shapes, with their central portions being concaved downward. In more detail, the two lower guide rails 263 comprised in the two respective shift mechanisms 26 are attached so as to be parallel to the X axis. By the roller units 262 shifting above and along the concave portions that are formed upon the lower guide rails 263, it becomes possible for the frame 2 to which the anti-vibration mounts 25 are fixed to shift along the X axis direction.

In order to keep the deflections of the second bottom surfaces 16 small, the lower guide rails 263 are attached at positions upon the second bottom surfaces 16 that are close to the inner wall surfaces 17. In other words, the gap between the two lower guide rails 263 in the direction orthogonal to the direction of shifting (the X axis direction) of the frame 2 (i.e. in the Y axis direction) is shorter than the dimension of the frame 2 in the widthwise direction, i.e. along the Y axis direction. As described above, the centers of the roller units 262 that shift upon and along the lower guide rails 263 and the centers of the anti-vibration units 25 are provided so as to coincide with one another. Since, due to this, the distance between the attachment centers in the Y axis direction of the anti-vibration units 25 that support the frame 2 becomes shorter as compared to the width of the frame 2 in the Y axis direction, accordingly it is possible to keep the deflection and the vibration generated in the bottom base plate 22 of the frame 2 low. This is desirable because, the shorter are the distances between the inner wall surfaces 17 and the central axes in the Z axis direction of the lower guide rails 263, the less it becomes necessary to make the second bottom surfaces 16 thick in order to make the overall structure sufficiently strong.

As shown in FIG. 6, in this embodiment, in order from the minus X axis direction, three shift control structures 264a, 264b, and 264c are attached to each of the two upper attachment plates 261. The shift control structures 264a are detachably attached to the upper attachment plates 261, and function as stoppers that temporarily regulate the shifting of the frame 2 along the X axis direction when, as described hereinafter, the frame 2 is pulled out along the X axis direction to the exterior of the chamber 1 by just a predetermined shift amount. These shift control structures 264a are provided at positions that correspond to this predetermined shift amount within the total shift amount by which the frame 2 can be pulled out to the exterior of the chamber 1. In this embodiment, this predetermined shift amount described above corresponds, for example, to about 25% of the length of the frame 2 in the X axis direction. In other words, when the frame 2 starts to shift toward the minus X axis direction, and when the frame has shifted through a distance that corresponds to 25% of the length of the frame 2 along the X axis direction so that a certain portion of the frame 2 is exposed exterior to the chamber 1, then the shifting of the frame 2 is controlled by the shift control structures 264a (refer to FIG. 4). In this position, leg members 9 that will be described hereinafter are attached by the operator to the lower portions of the roller units 262a, and the weight of the frame 2 is supported by these leg members 9 when the frame is shifted further in the minus X axis direction.

The shift control structures 264b function as stoppers for stopping the shifting of the frame 2 along the X axis direction when the frame 2 has been shifted along the X axis direction to the exterior of the chamber 1 by the total maximum shift amount possible, in other words to the shifting limit. In this embodiment, the total shift amount of the frame 2 that corresponds to the positions at which the shift control structures 264b described above are provided is equivalent, for example, to around 75% of the length of the frame 2 in the X axis direction (refer to FIG. 5).

It should be understood that the predetermined shift amount by which the shifting of the frame 2 is regulated by the shift control structures 264a are not to be considered as being limited to 25% of the length of the frame 2 in the X axis direction. This predetermined shift amount may be any exposure amount that makes it possible to attach the leg members 9 in safety in a state in which a portion of the frame 2 is exposed outside the chamber 1, and can be permitted to be up to half of the length of the frame 2 in the X axis direction. Furthermore, the total shift amount is not to be considered as being limited to, for example, 75% of the length of the frame 2 in the X axis direction; it could be any shift amount by which the frame 2 is exposed from the chamber 1 that entails no inconvenience when performing maintenance, inspection, servicing and so on of the various sections fitted to the frame 2.

The mechanism by which shifting of the frame 2 is temporarily restrained by the shift control structures 264a will now be explained with reference to FIG. 7. FIG. 7 is a perspective view of one end along the minus X axis of one of the shift mechanisms 26, in which a region R that is surrounded in FIG. 1 by a single dotted broken line is shown as magnified. This shift control structures 264a are detachably attached by screws 93, 94 to the upper attachment plate 261. A limiting member 80 is attached by screws 81, 82 to the end portion along the minus X axis of the lower guide rail 263 of this shift mechanism 26. When the frame 2 shifts along the direction of the minus X axis, along with the upper attachment plate 261 of the shift mechanism 26 that is provided integrally with the frame 2, the shift control structures 264a also shift along the direction of the minus X axis. When the shift amount of the frame 2 reaches the predetermined shift amount described above, the face 264 as of the shift control structure 264a facing toward the minus X axis comes into contact against the face 80s of the limiting member 80 that faces toward the plus X axis. As a result, the shifting of the frame 2 toward the minus X axis is regulated. In this state, the leg members 9 are attached by the operator, and, when the frame 2 is to be shifted further, the shift control structures 264a are taken off by the operator from the upper attachment plates 261 by removing the screws 93, 94, so that the upper attachment plates 261 are able to shift further, until the shift control structures 264b come into contact against the limiting members 80.

Furthermore, the shift control structures 264a also have structures for limiting motion in the Z axis direction, and for thus preventing unexpected inclination of the frame 2 or separation thereof from the second bottom surfaces 16. It would also be acceptable to attach braking members such as rubber members or the like to the shift control structures 264a, with the objective of rapidly performing stopping inclination or separation.

Next, the leg members 9 for supporting the frame 2 when it has been pulled out to the outside of the chamber 1 will be explained with reference to FIG. 6. The leg members 9 are constructed so as to be capable of being installed to the lower surfaces (i.e. to the surfaces thereof toward the minus Z axis side) of the upper attachment plates 261 in the neighborhoods of the roller units 262a. Attachment plinths 92 are provided at the end portions of the leg members 9 toward the plus Z axis side, and these are provided with screw holes so that they can be bolted to the upper attachment plates 261. For example, wheels 91 are attached at the end portions of the leg members 9 toward the minus Z axis side, so that it becomes possible to shift them along the surface where the chamber 1 is disposed. The leg members 9 are formed so that their lengths in the Z axis direction are substantially equal to the height from the surface that supports the chamber 1 to the lower surfaces of the upper attachment plates 261, and thus they are capable of supporting the frame 2. As a result, while supporting the frame 2, the leg members 9 are able to shift along the X axis direction along, the surface upon which the chamber 1 is placed, together with the frame 2.

With the X-ray apparatus according to the embodiment of the present invention described above, the following beneficial operational effects are obtained.

(1) It is arranged for the shift mechanism 26 to shift the frame 2 to which the X-ray source 5 is mounted and the anti-vibration units 25 that attenuate vibration applied to the frame 2 integrally with one another. In concrete terms, it is arranged for the second bottom surfaces 16 to support the shift mechanisms 26, and for the shift mechanisms 26 to support the frame 2 via the anti-vibration units 25. Accordingly it is possible to enhance the accuracy of X-ray measurement, since it is possible to reduce the negative influence exerted upon the results of measurement of the object to be measured S with X-rays by preventing vibration from the exterior of the chamber 1, or by preventing from transmitting vibration generated by the operation of the shift mechanism 26 influenced by vibration from the exterior of the chamber 1 to the frame 2. In particular since the moment of inertia is large when vibration is generated in the frame 2 to which the heavyweight X-ray source is mounted, accordingly difficulty is experienced in attenuating this vibration once it has been generated. Due to this, in this embodiment, even if vibration is generated that cannot be damped out by the anti-vibration units 25, it is possible to prevent this vibration from being encouraged by the shift mechanism 26 and so on and to prevent vibration from being transmitted to the heavy X-ray source. Furthermore, although the necessity of pulling out the X-ray source 5 from the chamber 1 arises during maintenance of the X-ray source 5 such as filament exchange or the like, the abovementioned shift mechanisms 26 have a construction that makes it possible also to pull out the anti-vibration units 25 along with the frame 26. Since the anti-vibration units 25 are always loaded with the same weight even when the frame 2 is pulled out from the chamber 1, accordingly it is possible to prevent lifting up or resilience of the anti-vibration units 25 originating in change of the load upon the anti-vibration units 25 due to change of the load upon the anti-vibration units 25, so that maintenance and servicing becomes simple and easy.

(2) The plurality of roller units 262 comprised in the shift mechanisms 26 are provided more toward the frame 2 than the lower guide rails 263, and it is arranged for the central axes in the vertical direction of the plurality of anti-vibration units 25 substantially to agree with the centers of the roller units 262. Accordingly, it is possible to enhance the accuracy of measurement of the object to be measured S by enhancing the beneficial anti-vibration effect, since it is possible to attenuate vibration originating in the structure of the shift mechanisms 26 or the like with the anti-vibration units 25 that are provided directly above the shift mechanisms 26. Furthermore, since the weight of the frame 2 acts upon the lower guide rails 263 and the second bottom surfaces 16 via the roller units 262 that are provided directly below the anti-vibration units 25, accordingly it is possible to suppress distortion of the upper attachment plates 261 and to perform shifting of the frame 2 in a smooth manner, as compared with a case in which the roller units 262 are not provided directly below the anti-vibration units 25.

(3) It is arranged for the X-ray source 5 to be mounted to the frame 2 within a range defined as being between the positions where the plurality of anti-vibration units 25 are attached to the frame 2, and for the anti-vibration units 25 to be provided more inward than the outer edge portions of the lower surface of the bottom base plate 22 of the frame 2.

Since as a result the X-ray source 5 which is high in weight and has a high resonant frequency is supported, accordingly it is possible to prevent vibration by the provision of the anti-vibration units 25 over a wider area, and it is possible to prevent any negative effect being exerted upon the results of measurement with X-rays of the object to be measured S.

(4) Two of the lower guide rails 263 are arranged in parallel with the X axis direction, which is the direction in which the frame 2 shifts, and it is arranged for the distance (i.e., the gap) in the Y axis direction between these two lower guide rails 263 to be shorter than the dimension of the frame 2 in the Y axis direction, which is the direction orthogonal to its shifting direction. As described above, the centers of the roller units 262 that shift upon the lower guide rails 263 and the centers of the anti-vibration units 25 are provided so as to agree with one another. Due to this, the distances in the Y axis direction between the centers where the anti-vibration units 25 that support the frame 2 are attached are shorter, as compared to the width of the frame 2 along the Y axis direction. Accordingly, it is possible to keep the deflection and the vibration set up in the bottom base plate 22 of the frame 2 small.

(5) It is arranged to provide a structure in which the leg members 9 for supporting the frame 2 can be installed below the anti-vibration units 25. In particular, in this embodiment, it is arranged for it to be possible to install the leg members 9 below the roller units 262 that are installed below the anti-vibration units 25. Thus, when the frame 2 has been pulled out from the chamber 1, since it is possible to support the weight of the frame 2 with the leg members 2 via the anti-vibration units 25 and the roller units 262, accordingly, even when the frame 2 is exposed out from the chamber 1 by the predetermined amount or more, it is still possible to prevent the occurrence of distortion in the upper attachment plates 261 and/or the lower guide rails 263, and it is possible to perform shifting of the frame 2 in a smooth manner. Moreover, since it is arranged for it to be possible to remove the leg members 9, accordingly, if a plurality of X-ray apparatuses 100 are used within the same workplace or the like, it is possible for the same pair of leg members 9 to be used in common between that plurality of X-ray apparatuses 100.

(6) It is arranged to provide the shift mechanisms 26 with the shift control structures 264 that, when the leg members 9 are to be installed, temporarily regulate shifting of the frame 2 to the position where it has been shifted by the predetermined shift amount within the total shiftable amount of the frame 2. Accordingly, during the job of installing the leg members 9, sudden shifting of the frame 2 along the X axis direction originating in vibration from the exterior or the like is prevented, so that it is possible to contribute to improvement of the working safety.

(7) With this frame 2 to which the X-ray source 5, the mounting unit 6, and the X-ray detector 7 are mounted, the greater portion of the body of the X-ray source 5, which is high in weight, hangs below the lower surface of the bottom base plate 22. The position of the barycenter of the frame 2 along the Z axis direction is near the bottom base plate 22. And, since the frame 2 is supported from the minus Z axis side by the anti-vibration mounts 25, accordingly, in the Z axis direction, the position of the barycenter of the frame 2 and the positions of the anti-vibration mounts 25 are close together, so that, by enhancing the beneficial effect of attenuating vibration from the exterior of the chamber 1, it is possible to enhance the accuracy of measurement of the object to be measured S. Furthermore, it is possible to stabilize the attitude of the frame 2 when the frame 2 is shifted along the X axis direction.

(8) It is arranged to mount the X-ray source 5, the mounting unit 6, the X-ray detector 7, and the X ray detector drive unit 8 to the frame 2 along the Z axis direction. In particular, the X-ray source 5 hangs down from the bottom base plate 22 of the frame 2. Due to this, the spaces SP2 and SP3 are defined at the lower surface of the frame 2 (i.e. at the minus Z axis side thereof). Since it is possible to dispose the X-ray source control device 3 and the stage control device 4 within these spaces SP2 and SP3, whereas in the prior art they were disposed externally to the chamber 1, accordingly, as compared to prior art apparatuses, it is possible to reduce the area upon the surface where the chamber 1 is set up for installation.

Furthermore, it would also be possible to install the image processing device 41 that is connected to the X-ray detector 7 and the reconstruction processing device 42 that is connected to the image processing device 41 and to the stage control device 4 within the space SP2 in which the stage control device 4 is disposed (refer to FIGS. 2, 4, and 5), and in this case there would be no requirement greatly to increase the area for installation, even if the system is configured as a CT apparatus.

The following variations are also within the scope of the present invention, and it would also be possible to combine one or a plurality of these variant embodiments with the embodiment described above.

(1) It would be acceptable to attach the guide rails to the anti-vibration units 25, to attach the attachment plates to the second bottom surfaces 16, and to attach the roller units 262 to the attachment plates. In this case, the roller units 262 would desirably be attached to the attachment plates so that, in the state in which the entire frame 2 is received in the chamber 1, the central axes of the anti-vibration units 25 in the vertical direction (i.e. in the Z axis direction) would pass through the roller units 262.

(2) Instead of the leg members 9 being installable, it would also be acceptable to arrange for the leg members 9 to have a folding construction, so that they can be received in the lower surface of the bottom base plate 22.

(3) It would be possible to attach encoders to each of the X axis shift mechanism 62, the Y axis shift mechanism 63, the Z axis shift mechanism 64, the rotation mechanism 81, and the X-ray detector shift mechanism that shifts the X-ray detector 7 along the circular arcuate stage 82, and thereby to acquire positional information for the mounting unit 6 and for the X-ray detector 7. Moreover, it would be possible to reconstruct the cross-sectional structure of the object to be measured S by acquiring projection image data, i.e. transmission X-ray images photographed by the X-ray detector 7, while acquiring corresponding position information. In this case, collaborative control of the X-ray detector 7 and the X-ray detector drive unit 8 would be performed by an image processing unit not shown in the figures, while the rotation shaft 815 would be controlled by the stage control device 4. And, if this is to be made into a CT apparatus as described above, then a reconstruction processing device 42 would acquire projection image data via the image processing device 41 while image capture for the object to be measured S would be performed by the X-ray detector 7 from a plurality of different directions. Moreover, the reconstruction processing device 42 would acquire the outputs from the encoders via the stage control device 4. And, on the basis of the projection image data and the outputs from the encoders, the reconstruction processing device 42 would be able to calculate the internal structure of the object to be measured S by a per se known Feldkamp back-projection method.

The present invention should not be considered as being limited to the embodiments described above; provided that the essential characteristics of the present invention are preserved, other implementations that are considered to fall within the range of the technical concept of the present invention are also to be included within its scope.

REFERENCE SIGNS LIST

1: chamber
2: frame
5: X-ray source
6: mounting unit
7: X-ray detector
9: leg member
16, 16a, 16b: second bottom surfaces
22: bottom base plate
25: anti-vibration unit
26: shift mechanism
41: image processing device
42: reconstruction processing device
61: stage
62: X axis shift mechanism
63: Y axis shift mechanism
64: Z axis shift mechanism
261: upper attachment plate
262: roller unit
263: lower guide rail
264: shift control structure

The invention claimed is:

1. An X-ray apparatus, comprising:
   an X-ray source that radiates X-rays upon an object to be measured;
   a frame upon which the X-ray attenuates vibration applied to the frame;
   a base plate unit that supports a shift mechanism; and
   the shift mechanism that shifts the frame and the anti-vibration mechanism integrally together.

2. The X-ray apparatus according to claim 1, wherein:
   the frame further comprises:
   a stage upon which the object to be measured is mounted; and
   an X-ray detector that detects X-rays that have been radiated from the X-ray source and that have passed through the object to be measured.

3. The X-ray apparatus according to claim 2, wherein:
   the shift mechanism supports the frame via the anti-vibration mechanism.

4. The X-ray apparatus according to claim 1, wherein:
   the shift mechanism comprises:
   a guide rail; and
   a plurality of shift members that relatively shift along the guide rail; and wherein:
   the shift members are positioned below the anti-vibration mechanism in the vertical direction.

5. The X-ray apparatus according to claim 4, wherein:
   the shift mechanism is adapted so that leg member for supporting the frame can be installed below the shift member.

6. The X-ray apparatus according to claim 5, wherein:
   the shift mechanism comprises a regulation member that, when the leg member is to be installed, temporarily regulates shifting of the frame to a position at a predetermined shift amount within the total shiftable amount of the frame.

7. The X-ray apparatus according to claim 4, further comprising:
   a chamber that houses the frame, and wherein:
   the base plate constitutes a portion of the chamber; and
   in a position in which the frame has been shifted by a predetermined shift amount, at least a portion of the frame is exposed from the chamber.

8. The X-ray apparatus according to claim 1, wherein:
   the anti-vibration mechanism is provided more inward upon a lower surface of the frame than an outer edge portion of the lower surface of the frame.

9. The X-ray apparatus according to claim 2, further comprising:
   a reconstruction unit that calculates the internal structure of the object to be measured on the basis of projection images of the object to be measured obtained when X-rays have passed through the object to be measured from a plurality of different directions while changing a relative position of the X-ray detector and the object to be measured.

* * * * *